United States Patent [19]

Finnah

[11] Patent Number: 5,464,595
[45] Date of Patent: Nov. 7, 1995

[54] METHOD AND MACHINE FOR DRAWING OFF FOODS AND DRINKS ASEPTICALLY

[75] Inventor: Josef Finnah, Ahaus, Germany

[73] Assignee: GEA Finnah GmbH, Ahaus, Germany

[21] Appl. No.: 164,605

[22] Filed: Dec. 9, 1993

[51] Int. Cl.$^6$ .................. A61L 2/00; A23B 3/00; A23L 3/16
[52] U.S. Cl. .................. 422/297; 422/25; 422/302; 422/307; 422/308; 426/521; 426/392
[58] Field of Search ...................... 422/297, 300, 422/302, 304, 307, 308, 198, 25; 165/30, 61, 65, 120; 426/521, 392

[56] References Cited

U.S. PATENT DOCUMENTS

| | | | |
|---|---|---|---|
| 967,076 | 8/1910 | Spenle | 165/61 X |
| 1,999,832 | 4/1935 | Dreffein | 165/65 X |
| 3,626,480 | 12/1971 | Takel et al. | 165/61 |

Primary Examiner—Robert J. Warden
Assistant Examiner—Christopher Y. Kim
Attorney, Agent, or Firm—Jordan and Hamburg

[57] ABSTRACT

In a method for aseptically drawing off food and drink into plastic containers, the container sheet is plasticized for molding the containers and subsequently molded in a sterile environment, after which the container recesses are filled and closed off by means of a lid sheet. For this method and before the filling process, the container sheet is acted upon in a longitudinal segment by means of steam for sterilization purposes and is cooled on its side opposite to the steam-impingement area. Before it is supplied to the container sheet, the lid sheet is sterilized. After they are sterilized and until they are combined, the lid sheet and the container sheet are kept in germ-free surroundings. In order to be sterilized on both sides, the container sheet is acted upon reciprocally in the flat state before it is molded, with steam in two consecutive treatment processes in, in each case, the same length segment, and, at the same time, cooled.

11 Claims, 7 Drawing Sheets

METHOD AND MACHINE FOR DRAWING OFF FOODS AND DRINKS ASEPTICALLY

The invention relates to a method and a machine for drawing off foods and drinks aseptically.

BACKGROUND OF THE INVENTION

For a known method (Verpackungsrundschau 33 (1982), No. 8, pages 47–50; European patent 0 045 389 B1), a container is formed by thermoforming the container sheet and then acting upon it with steam, which brings about the sterilization of the container sheet on the filling side. For this process, the back container sheet is cooled by the wall of the molding tool. The aluminum lid sheet is sterilized on both sides as it passes through a steam chamber. The sterilization of the container sheet, accomplished in this way, leaves something to be desired and does not exclude the dangers of re-infection. In the case of plastic lid sheets, the simultaneous action of steam on both sides leads to distortion phenomena. Furthermore, it is known that, for sterilization purposes, container sheet, before it is shaped, can be pulled through a hydrogen peroxide bath, which brings about the sterilization of the sheet on both sides (DE 30 28 208 A1).

SUMMARY OF THE INVENTION

It is an object of the invention to provide a method and a machine for drawing off foods and drinks aseptically into plastic containers by means of a gentle and reliable sterilization of the space of the container accommodating the food or drink. Said method and machine are to be usable in drawing-off installations, which operate at a high cycling rate.

The inventive method and machine enable the sterilizing effect of steam to be utilized in a simple and inexpensive manner on both sides of sheets, consisting of plastic, over a sufficiently long period of action, since the sheets can be treated with little effort over a period of several working cycles of the drawing-off equipment and, with that, can be handled for a sufficiently long period of time, for killing germs reliably. Sterilizing on both sides avoids any entrainment of germs in the drawing-off area and, with that, ensures a reliable, aseptic drawing-off of products into the containers.

With the reciprocal action of steam and cooling in two consecutive processes on flat, longitudinal sections of the sheets, it is possible to act with relatively high temperatures on the sheet surface and achieve a complete surface sterilization, without adverse effects on the form stability of the sheets even when the steam acts on them for a longer period.

The sterilization of sheets in a process separated from other operating processes opens up the possibility of working with different forward feed speeds, so that short cycling times can be achieved in the main station, while the steam nevertheless acts on the respective sheet side for a period of time adequate for sterilization.

With respect to further advantages and details of the invention, reference is made to the following description and to the drawing, in which an embodiment of the object of the invention is illustrated in greater detail diagrammatically.

DESCRIPTION OF THE PREFERRED EMBODIMENTS

Figure 1:
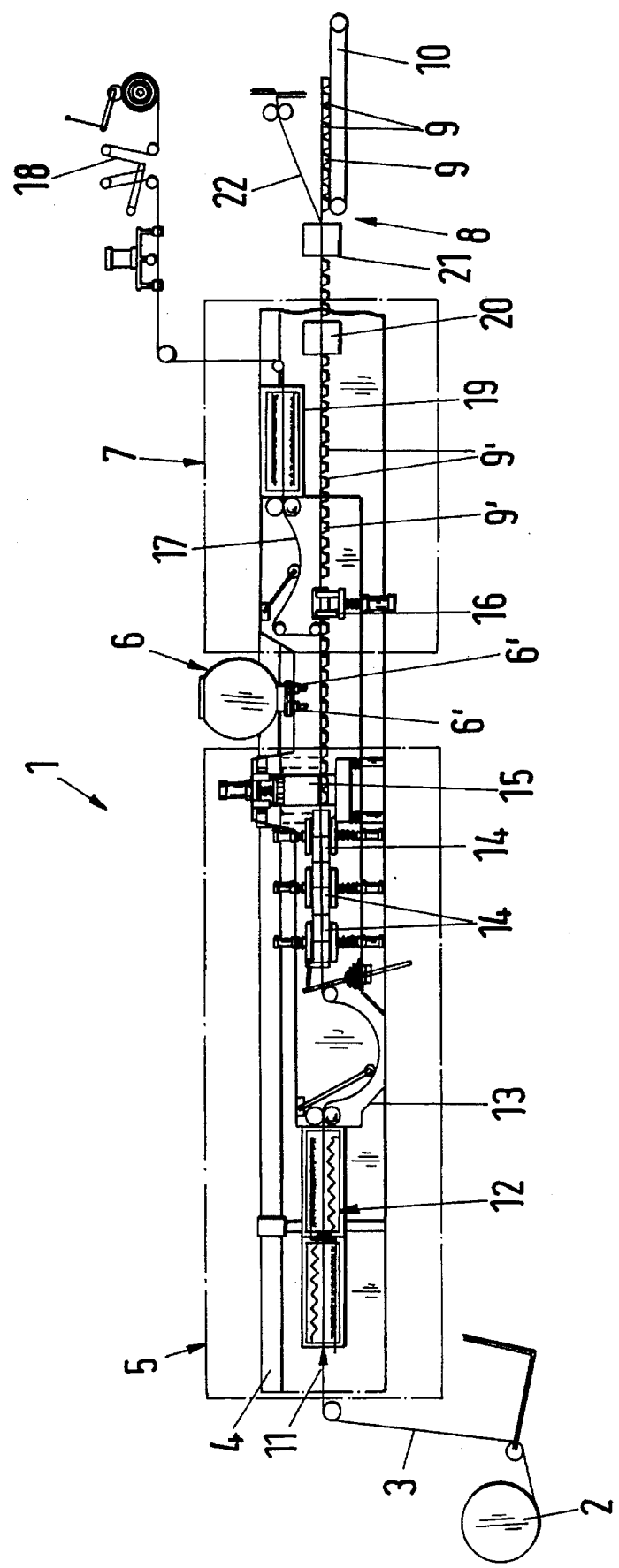
FIG. 1 shows a basic representation of a packaging machine for drawing off aseptically pursuant to the invention.

A drawing-off machine is shown in FIG. 1. It is labeled 1 as a whole and is supplied with a container sheet 3 that is unrolled from a supply roll 2. Within a machine frame 4 of the drawing-off machine 1, the container sheet 3 passes through a front area 5, drawing-off equipment 6 and then through a rear area 7. In an end region 8, individual, filled plastic containers 9 are transferred to a conveyor belt 10.

In the feeding direction of the container sheet 3, which is indicated by an arrow 11, sterilization equipment 12, which discharges directly into a sterile tunnel 13 extending as far as the rear area 7, three contact hot plates 14 and a container-molding station 15 are disposed consecutively in the front area 5. Adjoining this, behind the drawing-off equipment 6 protruding with at least its filler organs 6' into the sterile tunnel 13 in the rear area 7 of the drawing-off machine 1, there is pre-sealing-on equipment 16 into the operating area of which in the sterile tunnel 13, a lid sheet 17 is supplied from a lid sheet supply roll 18 over sterilization equipment 19. The container sheet 3, connected in the pre-sealing-on equipment 16 along its outer edges with the outer edges of the lid sheet 17, leaves the sterile tunnel 13 with filled container parts 9' in the advance direction 11 and is fully sealed with the lid sheet 17 by means of sealing equipment 20, so that thereupon the plastic containers 9, moved along by the conveyor belt 10, can be isolated in the end region 8 by means of a punch 21 and separated from the punch lattice sheet 22 that is formed as waste.

Figure 2:
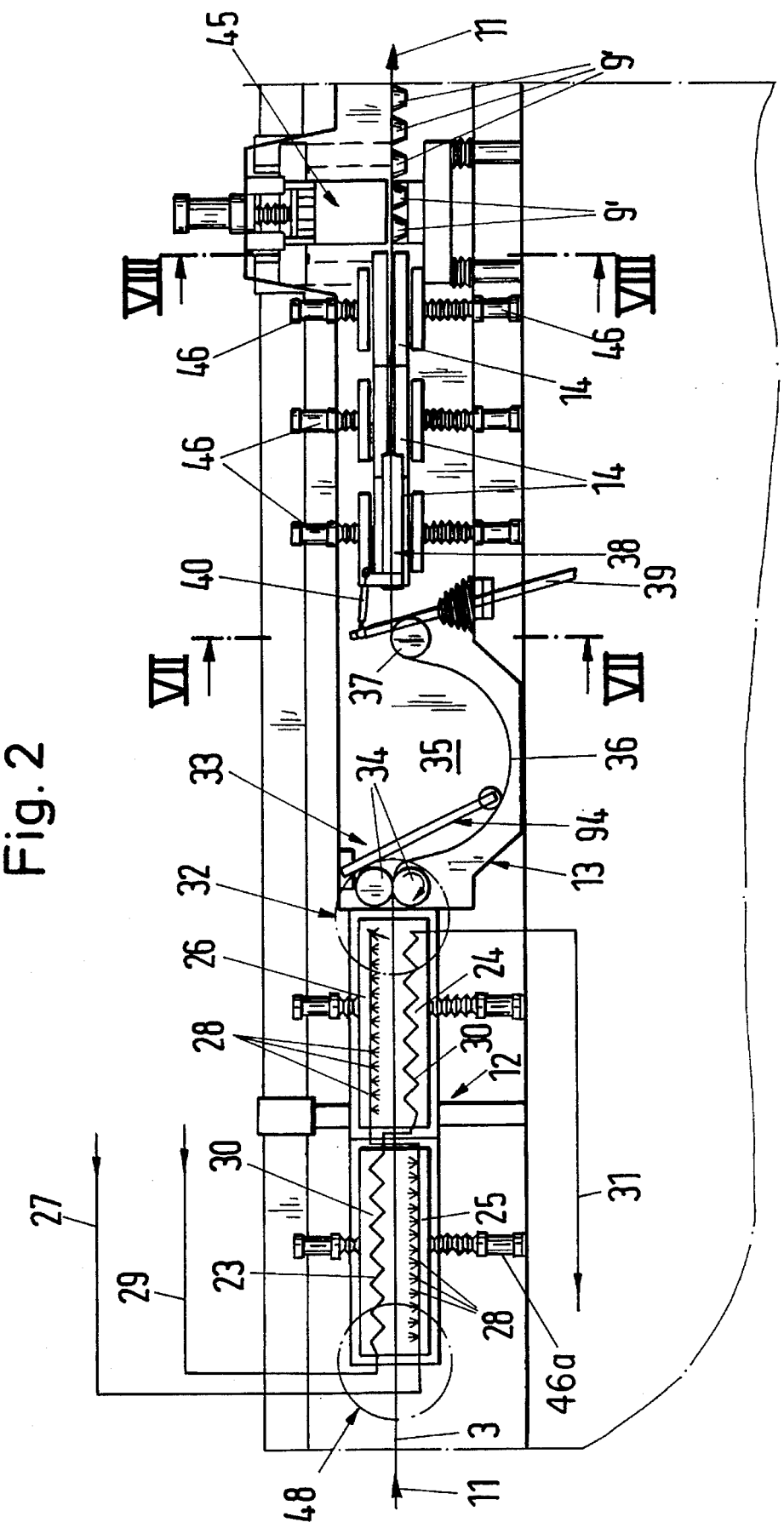
FIG. 2 shows an enlarged sectional representation of sterilization equipment for the container sheet with an adjoining sterile tunnel in accordance with Section 5 of FIG. 1.

The front area 5 of the drawing-off machine 1 is shown as an enlarged cutout in FIG. 2. In this representation, the advantageous development of the sterilization equipment 12, with two consecutively disposed groups of plate-shaped molding tool parts, which, in each case, can accommodate a longitudinal section of the flat container sheet 3 between themselves, becomes clear. In each case, one molding tool part of each group is constructed as a contact cooling plate 23 or 24 and the opposite molding tool part is constructed as a steam distributing plate 25 or 26. The molding tool parts, preferably only the respectively lower molding tool parts 24, 25, can be brought by means of a lifting mechanism (46a) from their operating position shown into an open position, which enables the container sheet 3 to be advanced in the direction of arrow 11. By means of locking equipment, they can be fixed to one another in their operating position (FIG. 2).

The sterilization equipment 12 is supplied by way of a feed line 27 from a steam generator (not shown) in such a manner with steam, that a sufficient amount of steam can be supplied in the area of the respective steam distributing plates 25 or 26 over a number of outlet openings 28 distributed over a surface facing the container sheet 3 and can be distributed over the whole of the opposite container sheet surface. The outlet openings 28 can, in this connection, advantageously be constructed as nozzles, with which the steam is directed to the respective side of the flat container sheet 3. In this flat state, the container sheet 3 experiences first on a section of its upper side and then, in a second treatment process in the same section, on its underside, a complete steam sterilization, the uniformity of which cannot be affected by any unevennesses or recesses.

Simultaneously with the action of steam from the steam distributor plates 25, 26, an appropriate cooling medium is supplied over a further feed line 29 to the contact cooling plates 23, 24 and, after passing through cooling loops 30, discharged over a recycling line 31, so that the cooling medium can be cycled through a heat exchanger (not shown).

Cooling the one side of the container sheet 3 during the simultaneous steam sterilization of the opposite side avoids affecting the sheet material adversely through overheating even at higher temperatures, which exceed the softening temperature, such as 120° C. to 145° C., appreciably, and during longer periods of action, such as 8 seconds or more. This is the case also for sheets of different thicknesses.

Together with its two molding tool groups 23, 25 and 24, 26, the sterilization equipment 12 forms a totally enclosed unit, which is disposed immediately in front of the sterile tunnel 13 of the drawing-off machine 1 that is charged with sterile air. In a region 32, the container sheet 3 is transferred into the sterile tunnel 13 in such a way as to be shielded from the surroundings. Such a procedure ensures that the container sheet 3, sterilized in two consecutive treatment steps, is already free of germs before it is plasticized and shaped into containers and entrainment of germs into the sterile tunnel 13 is avoided, owing to the fact that a continuous, germ-free interior space is formed by the sterile air blown into the sterile tunnel 13.

For moving the container sheet 3 through the sterilization equipment 12, a separate advancing mechanism 33, which has separately driven advancing rollers 34, is provided in the inlet region of the sterile tunnel 13. These advancing rollers 34 cause the container sheet 3 to move independently of the advancing motion of the container sheet 3 in the subsequent regions of the drawing-off machine 1. Preferably, the advancing mechanism 33 brings about at time intervals of several, preferably four, working cycles of the drawing-off machine (that is, for a working cycle of, for example, 2 seconds, at time intervals of, for example, 8 seconds), an advance, which is at least essentially the same as the advance of the container sheet 3 in the subsequent part of the drawing-off machine 1 within the same time intervals. For an advance at time intervals of four working cycles, the advance, produced by the advancing rollers 34, accordingly amounts to four-times the advance of the container sheet 3 during one operating cycle of the drawing-off machine 1 in the region behind the sterilization equipment 12.

For this purpose, the sterile tunnel 13 behind the advancing rollers 34 is provided with an expanded accommodating space 35, which can accommodate a supply loop 36 of the container sheet 3 corresponding approximately to one advance of the mechanism 33. From this region of the supply loop 36, the container sheet 3 passes over a deflection roller 37 into the region of the contact hot plates 14 and is moved on from there cyclically by two advancing beams 38 (FIG. 7), which are driven by a main driving mechanism (not shown) of the drawing-off machine 1 and form the main advancing mechanism of the drawing-off machine 1.

The two advancing beams 38 take hold of the two longitudinal edges of the container sheet 3. For this purpose, each advancing beam 38 is connected with a driving link comprising a transverse bar 40 of a driving lever 39 and comprises lifting drives between an upper part 41 and a lower part 42, which can take hold of the edge of the container sheet 3 with connecting strips 41' and 42' and carry it along for an advancing motion in the direction of arrow 11. The advancing beams 38 are supported at both ends on roller-type guides 43 so that they can move back and forth.

In the region of the three contact heating plates 14, the container sheet 3 is plasticized stepwise. At the conclusion of an advancing motion, upper plates 44 and lower plates 44' (FIG. 7), movable for one operating cycle of the drawing-off machine 1, engage the container sheet 3 and, before the start of a following advancing motion, disengage from it once again by way of assigned compressed air cylinders 46. In the phase in which the container sheet 3 is plasticized by means of the contact hot plates 14, temperatures can be reached in the region of the surface of the container sheet 3, which in turn can bring about a sterilization effect.

In the container-molding station 15, the container parts 9', under the action of an appropriate thermoforming molding tool 45 (FIG. 8), are shaped from the plasticized container sheet 3 and then advanced into the region of the filling equipment 6.

By means of the sterilization equipment illustrated in FIGS. 1 and 2, the container sheet 3 can be heated superficially in the respective steam-impingement area to about 120°–145° C. Due to the simultaneous cooling of the opposite surface of the container sheet 3 by means of the respective contact cooling plates 23, 24, sufficient heat can be withdrawn, so that the temperature of the cooled surface of the container sheet 3 does not exceed about 60° C., so that thermal deformations of the container sheet 3 are precluded. The holding time in the region of the respective steam impingement of preferably 5 to 10 seconds merely requires an appropriate dimensioning of the length of the sterilization equipment 12 in the advance direction 11, which can be realized at little expense.

Figure 3:
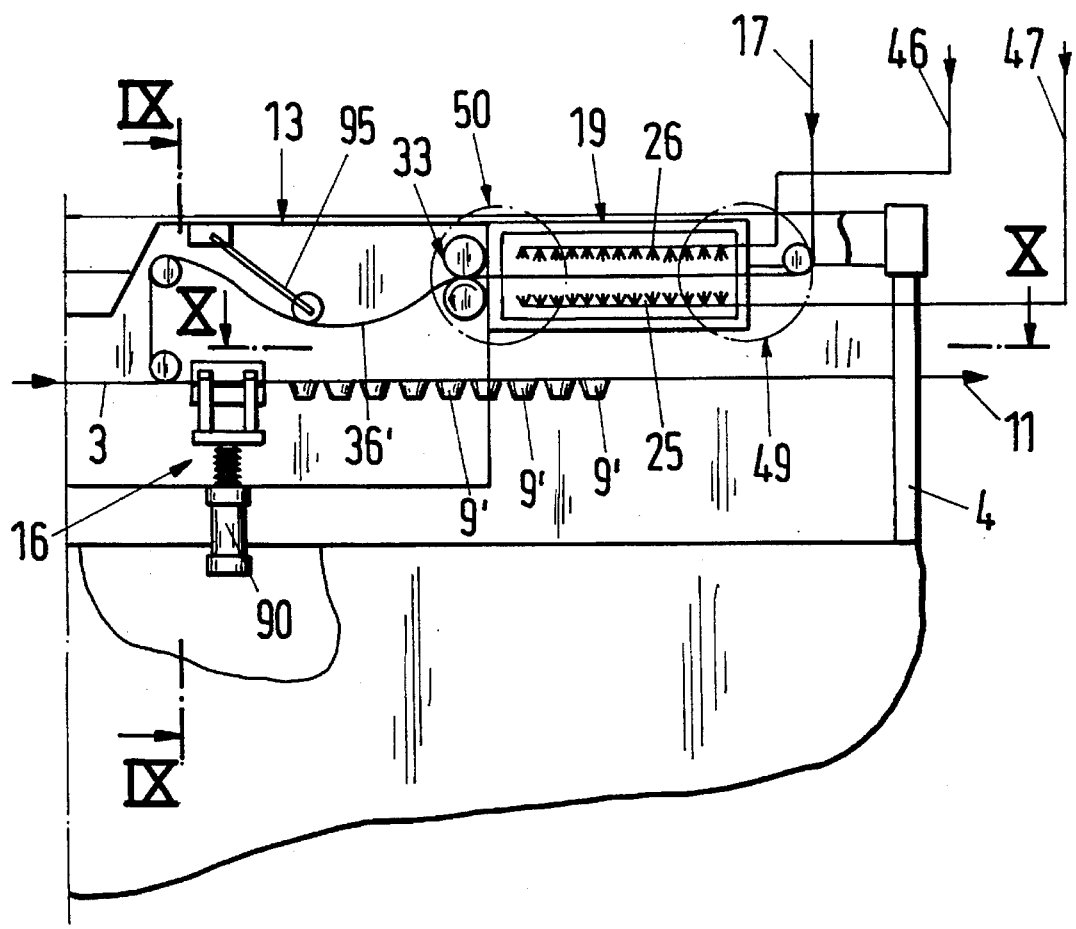
FIG. 3 shows an enlarged basic representation of a lid sheet sterilization equipment of Section 7 of FIG. 1, assigned to the sterile tunnel.

The rear region 7 of the drawing-off machine 1, which is shown on a larger scale in FIG. 3, elucidates the sterilization equipment 19 in the region in which the lid sheet 17 is supplied. The construction of the sterilization equipment 19 is similar to that suitable for an aluminum lid sheet or foil 17 and, because of the heat resistance of the material, permits steam to impinge simultaneously on both sides. The steam is supplied over appropriate feed lines 46 and 47 to two mutually opposite steam distributing plates 25, 26. The sterilization, which takes place before entry into the sterile tunnel 13, can in this case be carried out without cooling measures. Here also, the arrangement of the sterilization equipment 19 immediately before the rear end of the sterile tunnel 13 reliably ensures the germ-free entry of the lid sheet 17 into the sterile tunnel 13 and, in this, to the lid pre-sealing equipment 16.

Figure 4:
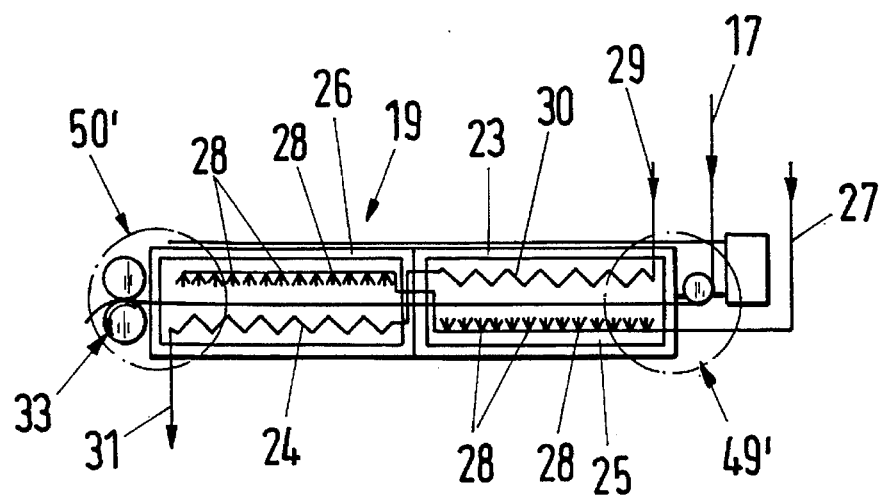
FIG. 4 shows an enlarged, detailed representation of sterilization equipment for the lid sheet, similar to that of FIG. 3.

For lid sheets 17 of a plastic material, sterilization equipment 19' is used, the construction of which corresponds to that of the sterilization equipment 12 of the container sheet 3. Such a version is shown in FIG. 4, in which the parts, similar in construction to those of the sterilization equipment 12 of FIG. 2, have been given the same reference numbers. With regard to the construction and function of the sterilization equipment 19', reference is made to the comments relating to the sterilization equipment 12. What has been stated in relation to FIG. 2 also applies correspondingly for the lid sheet driving mechanism, the loop formation, etc.

Figure 5:
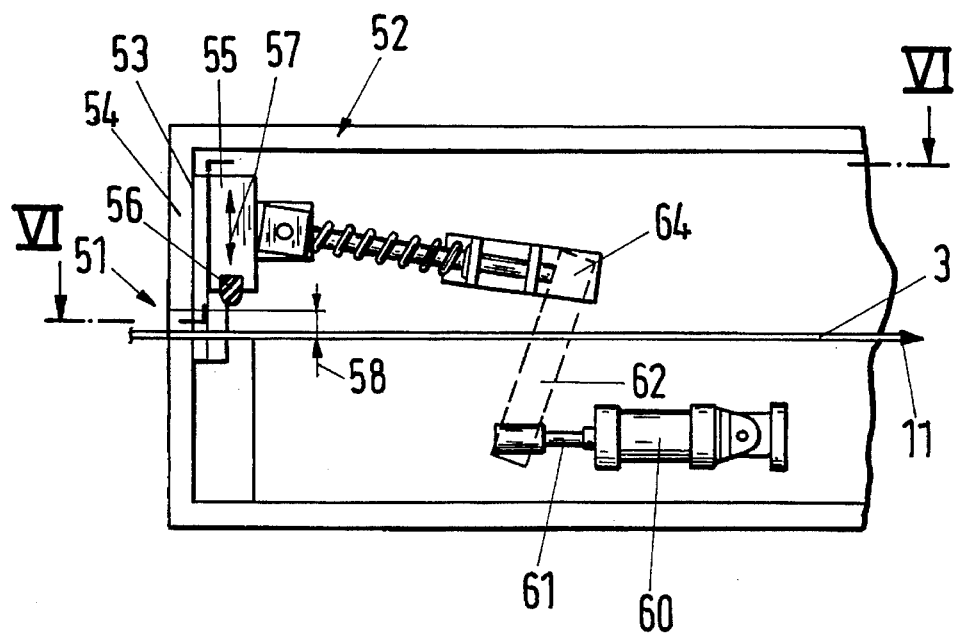
FIG. 5 shows an enlarged part representation of Section 5 of FIG. 1 in the area of the inlet for the container sheet into the sterilization equipment.
Figure 6:
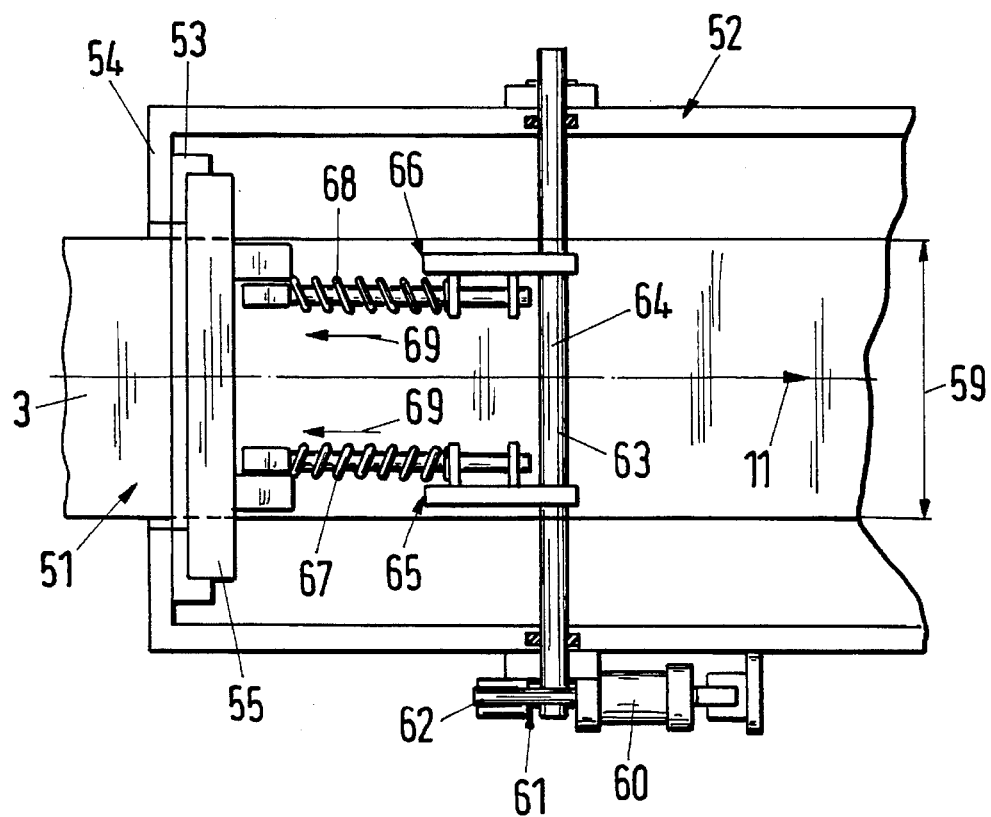
FIG. 6 shows a partially cut representation of the inlet into the sterilization equipment along the sectional line VI—VI of FIG. 5.

A seal, which prevents entry of germ-containing surrounding air, may be necessary for reliably keeping the container sheet 3 and the lid sheet 17 sterile in the sterile tunnel 13. This is so primarily for the regions 48 (FIG. 2) and 49 or 49' (FIGS. 3 and 4). Seals may also be provided at the transitions in the regions 32 (FIG. 2) and 50, 50' (FIGS. 3 and 4). An example of the design of the seal for a feed opening 51 for the container sheet 3 or the lid sheet 17 to the sterilization equipment 12, or 19, 19', suitable, for example, for the regions 48, 49, is shown in FIGS. 5 and 6. In principle, such a seal can also be provided at the transitions in the regions 32, 50, 50'.

FIGS. 5 and 6 illustrate in two views a housing 52, which surrounds the sterilization equipment 12 and 19 or 19' as a whole. In the region of the feed opening 51, a guide fillet 53 is disposed, which is braced on the inside at the wall 54 of the housing 52 and continues the feed opening 51 with an opening. At the guide fillet 53, there is a sealing beam 55 which, when pressed against the guide fillet 53, engages this so as to form a seal. A sealing fillet 56, particularly one of temperature-resistant silicone rubber, lays itself on the container sheet 3 during the downwards motion of the sealing beam 55 in the direction of arrow 57 in such a way, that the feed opening 51 is closed off to the full extent of its height 58.

In the region of the feed opening 51, the sealing beam 55 protrudes over the edge of the container sheet 3, the width of which is labeled 59. Said sealing beam 55 can be moved by means of a lifting cylinder 60, such as a compressed air cylinder. The lifting motion of the piston rod 61 is transferred over a lever 62, which is hinged to said piston rod 61, to a transfer shaft 63, which is firmly connected with said lever 62 and reaches through the housing 52. The oscillation of said transfer shaft 63 about the center line 64 is transferred to connecting rods 65, 66, which bring about the up and down motion of the sealing beam 55 in the directions corresponding to arrow 57 (FIG. 5).

In each case, a compression spring 67, 68, which presses the connecting rods, and with that, the sealing beam 55 against the guide fillet 53 in the direction of arrow 69, is assigned to the connecting rod 65, 66.

Figure 7:
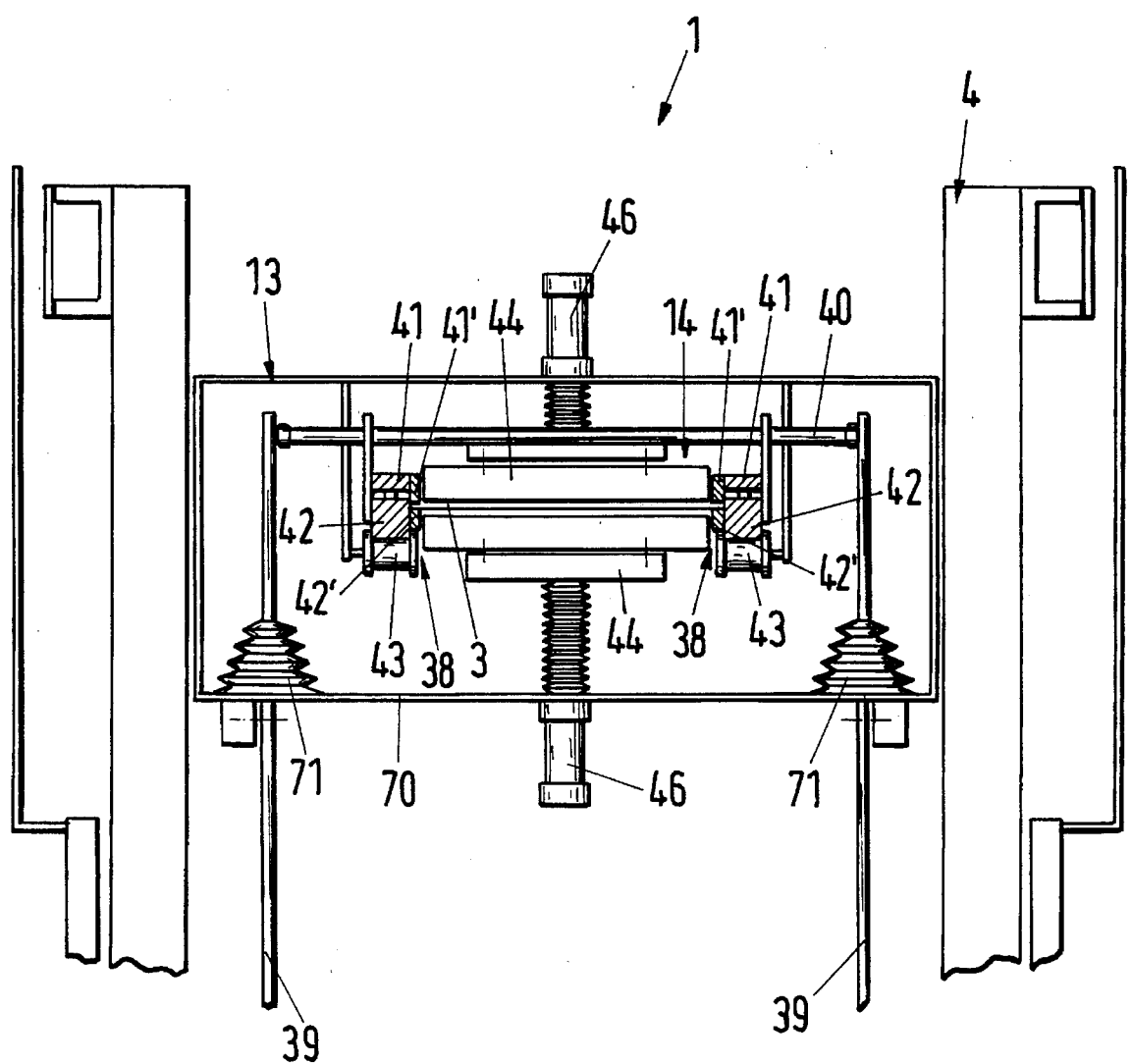
FIG. 7 represents a region of the sterile tunnel along the line VII—VII of FIG. 2.

FIG. 7 shows that the driving levers 39, which are provided for operating the advancing beam 38 and reach through the bottom 70 of the sterile tunnel 13, as well as the piston rods of the driving cylinders 46 for the hot plates 44, 44' reaching into the sterile tunnel 13, are each provided with a reliable seal by means of bellows 71.

Figure 8:
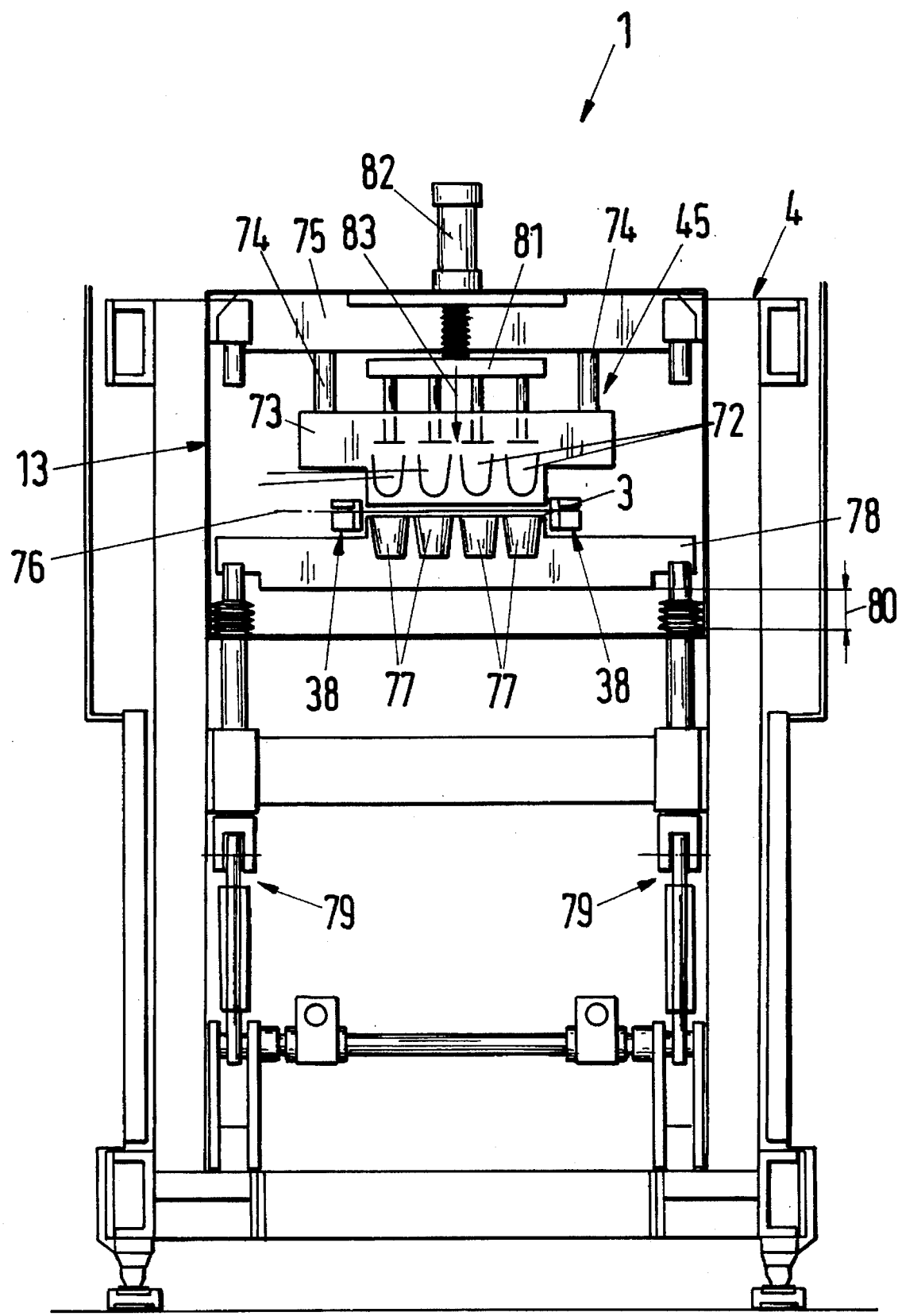
FIG. 8 shows an enlarged representation of an area of the container molding section along the line VIII—VIII of FIG. 2.

FIG. 8 illustrates, by way of example, a thermoforming molding tool 45, with four container molding tools 72, which are guided in an upper tool 73, which is braced in stationary fashion by struts 74 against a yoke 75 in the sterile tunnel 13. Below an advancing plane 76, in which the container sheet 3 moves, there are container-molding nests 77 in a lower tool 78 assigned to the respective container-shaping molding tools 72. Relative to the stationary upper tool 73, the lower tool 78 can be lowered by means of a driving lever system 79 engaging the edge by such an amount 80 out of the operating plane that, when the container sheet 3 is moved in the direction of arrow 11 (FIG. 2), the molded container parts 9' can be advanced freely to the drawing-off equipment 6 (FIG. 2). The still-flat container sheet 3, plasticized by the contact hot plates 14, can now be molded simultaneously in the area between the container molding tools 72, 77 to form containers in a new operating cycle.

For molding containers, the container molding tools 72 are lowered by means of a common supporting plate 81, through the agency of a driving cylinder 82 above, in the molding direction 83 onto the container sheet 3 and into the mold nests 77 covered by said container sheet 3. After this preliminary mechanical molding, the process of molding the container parts 9' is completed by means of sterile, compressed air.

Figure 9:
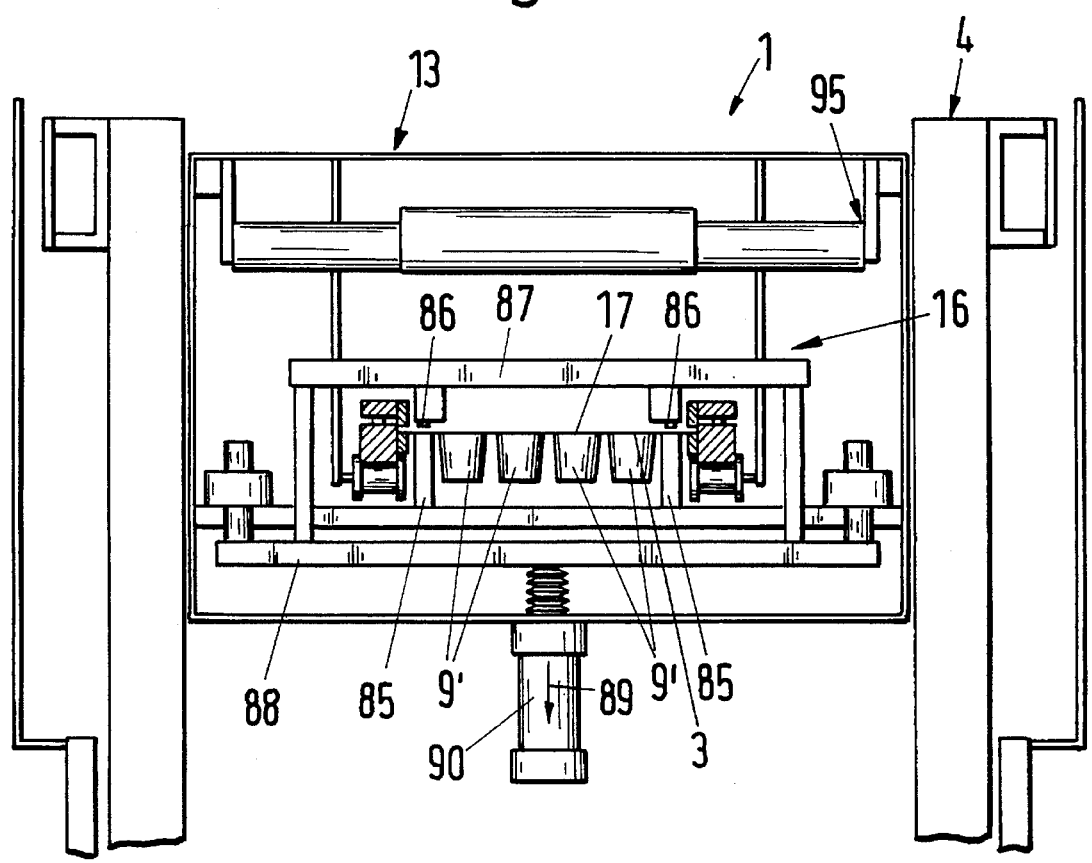
FIG. 9 shows an enlarged representation of an area of the lid sealing-on equipment along the line IX—IX of FIG. 3

The container sheet 3, with its molded container parts 9', is advanced into the region of the drawing-off equipment 6 (FIG. 1), where the container recesses are filled. From there, the filled container parts 9' reach the region of the lid pre-sealing equipment 16, which is shown in an enlarged cross section in FIG. 9. In station 16, the edge of the container sheet 3 lies on supports 85, opposite each of which a sealing element 86 is disposed. The sealing elements 86 are connected over a bridge part 87 with a lifting beam 88. As said lifting beam 88 is moved by means of a driving cylinder 90 in the direction of the arrow 89, the sealing elements 86 are lowered onto the upper side of the edge of the lid sheet 17, which has meanwhile been supplied and overlaps the container sheet 3 and the edge of the lid sheet 17 is combined with the edge of the container sheet 3 during the advancing cycle.

Figure 10:
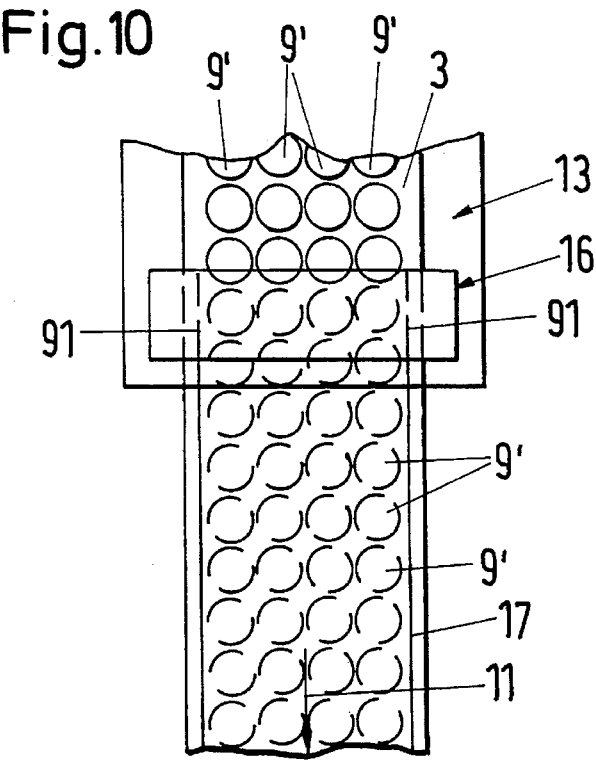
FIG. 10 shows a representation of an area of the pre-sealing-on equipment along the line X—X of FIG. 3.

In a diagrammatic plan view of the pre-sealing area, FIG. 10 shows that the lid sheet 17, before it passes through the end of the sterile tunnel 13, is connected at the edges by means of a sealing seam 91 with the container sheet 3 in such a manner that, on exiting into the surroundings, a sterile seal for the food and drink in the container 9' is retained. Any further processing to individual containers 9 or groups of containers (not shown) is then possible after the sealing station 20 (FIG. 1).

A scanner, by means of which the lengths of the loop can be determined and, if necessary, be corrected, can be assigned to the supply loops 36 for the container sheet 3 or the supply loops 36' for the lid sheet 17. For this purpose, for example, a scanner 94 or 95 (FIGS. 2 and 3) can be provided in the form of a switching rocker which, when a given deflection is reached, emits a control signal for correcting the loop length by means of the driving mechanism 33.

I claim:

1. Apparatus for sterilizing a sheet of plastic which is to be molded into a container part to be used in packaging a food product, the apparatus comprising:

first steam-discharging means for applying steam to one side of one segment of a sheet;

first cooling means for cooling the other side of said one segment of said sheet;

said first steam-discharging means applying steam to said one side of said one segment simultaneously as said first cooling means cools said other side of said one segment;

second steam-discharging means applying steam to said other side of a juxtaposed segment of said sheet;

second cooling means cooling said one side of said juxtaposed segment of said sheet;

said second steam-discharging means applying steam to said other side of said juxtaposed segment simultaneously as said second cooling means cools said one side of said juxtaposed segment.

2. Apparatus according to claim 1 wherein said first steam-applying means applies steam to said one side of said one segment simultaneously as said first cooling means cools said other side of said one segment.

3. Apparatus according to claim 2 wherein said second steam-discharging means applies steam to said other side of said juxtaposed segment simultaneously as said second cooling means cools said one side of said juxtaposed segment.

4. Apparatus according to claim 3 wherein said first steam-discharging means and said first cooling means are operable simultaneously with said second steam-discharging means and said second cooling means.

5. Apparatus according to claim 1 wherein said one segment and said juxtaposed segment each have an equal longitudinal segmental length, and means for advancing said sheet a longitudinal distance corresponding to said segmental length such that a plurality of sheet segments are periodically and sequentially sterilized on both sides by said first and second steam-applying means.

6. Apparatus according to claim 1 wherein said first and second steam-discharging means comprise a plurality of steam outlet openings distributing steam onto said one and said other segments, respectively.

7. Apparatus according to claim 6 wherein said outlet openings comprise outlet nozzles.

8. Apparatus for sterilizing a sheet of plastic which is to be molded into a container part to be used in packaging a food product, the apparatus comprising:

first steam-discharging means for applying steam to one side of one segment of a sheet;

first cooling means for cooling the other side of said one segment of said sheet;

second steam-discharging means applying steam to said other side of a juxtaposed segment of said sheet;

second cooling means cooling said one side of said juxtaposed segment of said sheet;

enclosure means for enclosing from the environment said first steam-discharging means, said first cooling means, said second steam-discharging means and said second cooling means;

a sterilized tunnel;

advancing means for advancing said one and said juxtaposed segments to said sterilized tunnel after being sterilized by said first heat applying means and said second heat applying means in said enclosure means;

forming means in said tunnel for forming said sheet into food containers for containing a food product;

said advancing means comprising first feeding means for feeding said sheet through said enclosure means, and second feeding means for feeding said sheet through said tunnel, said first feeding means being operable independently of said second feeding means.

9. Apparatus according to claim 8 further comprising third feeding means for feeding a lid sheet to said tunnel, combining means for combining said lid sheet with said container sheet in said tunnel, said first, second and third feeding means feeding said container sheet and lid sheet, respectively, in synchronous and periodic advance and stop cycles.

10. Apparatus according to claim 8 further comprising loop-producing means in said tunnel for providing a container sheet supply loop in said container sheet in said tunnel.

11. Apparatus for sterilizing a sheet plastic which is to be molded into a container part to be used in packaging a food product, the apparatus comprising:

first steam-discharging means for applying steam to one side of one segment of a sheet;

first cooling means cooling the other side of said one segment of said sheet;

second steam-discharging means applying steam to said other side of a juxtaposed segment of said sheet;

second cooling means cooling said one side of said juxtaposed segment of said sheet;

advancing means for passing said container sheet generally horizontally between said first steam-discharging means and said first cooling means and generally horizontally between said second steam-discharging means and said second cooling means; and operable means for effecting relative vertical movement between said first steam-discharging means and said first cooling means and for effecting relative vertical movement between said second steam-discharging means and said second cooling means.

* * * * *